United States Patent [19]

Etheredge, III

[11] Patent Number: 5,308,609

[45] Date of Patent: May 3, 1994

[54] PROPHYLAXIS FOR KERATINOUS MATERIALS

[76] Inventor: Robert W. Etheredge, III, 5 Oakhill Rd., Natick, Mass. 01760

[21] Appl. No.: 44,025

[22] Filed: Apr. 8, 1993

Related U.S. Application Data

[63] Continuation-in-part of Ser. No. 832,898, Feb. 10, 1992, abandoned.

[51] Int. Cl.$^5$ ................................................. A61K 7/04
[52] U.S. Cl. ....................................... 424/61; 424/71; 514/846
[58] Field of Search .................... 424/61, 71; 514/846; 128/65

Primary Examiner—Paul R. Michl
Assistant Examiner—William E. Benston, Jr.
Attorney, Agent, or Firm—Alvin Isaacs

[57] ABSTRACT

Compositions are disclosed for protecting keratin-containing substances in the body, e.g. skin, nails and especially hair, from damage and for helping to restore the damaged keratinous material to a healthy state. In one embodiment the compositions will comprise a liquid fatty acid vehicle containing at least a long chain alkane for bonding hydrophobically to keratin.

25 Claims, No Drawings

PROPHYLAXIS FOR KERATINOUS MATERIALS

RELATED APPLICATION

This application is a continuation-in-part of my application Ser. No. 07/832,898 filed Feb. 10, 1992 and now abandoned.

BACKGROUND OF THE INVENTION

This invention relates to prophylaxis for keratinous materials, and more particularly to novel cosmetic formulations for hair, skin and other keratinous body materials.

Recent research as reported in the literature has shown that hair and skin suffer substantial damage from many sources. Keratinous assemblies can be damaged by environmental influences such as ultraviolet radiation, exposure to chlorine, and/or pH extremes. Hair can additionally suffer substantial damage from mechanical insult from extension, torsion, bending, and compression forces sufficient to cause permanent deformation as well as chemical damage from hair relaxants, bleaches and colorants, and even shampoo ingredients. This damage can range from depletion of endogenous and exogenous lipids and lipid complexes to structural damage such as the physical damage previously mentioned.

Since the present invention is particularly directed to compositions for treating hair to prevent damage thereto and/or to help restore healthy hair which has been damaged, the invention will be discussed in detail hereinafter by reference thereto.

Formulations for treating hair are of course well known in the art. For example, the shelves in pharmacies and other stores selling personal care items are replete with shampoos, conditioners and the like which are said to provide certain beneficial results. While by no means intended to represent a complete survey of the hair treatment products currently available, the following may be taken as illustrative: HUILE d'ALES (Laboratoires Phytosolba of Paris, France), a base of essential plant oils said to be used for dry, damaged hair; PHYTOSQUAME (Laboratoires Phytosolba) stated to contain an ingredient, Chaulmoogra oil, for its anti-exfoliation property; "COLORVIVE TECHNICARE" of L'Oreal which is said to repair frayed ends; "RAVE" of Cheesebrough-Ponds, said to be an all-in-one shampoo for cleaning and conditioning damaged, permed or colored hair; Freeman Botanical Hair Therapy Shampoo for dry, brittle or damaged hair (Freeman Cosmetic Corporation); "Infusion 23" of Duart Laboratories which is said to protect hair cuticles against split ends; so-called "hot oil" formulations such as "Alberto VO5" hot oil shampoo of Alberto-Culver which references U.S. Pat. No. 4,061,150 to be discussed hereinafter; and "Faberge Organics" of Faberge Company which is said to penetrate the hair shaft to build stronger hair within.

While a discussion of the ingredients listed on the containers of the above-mentioned products would render this description unnecessarily prolix, mention of the "Faberge Organics" product is of interest for its detailed formulation: water; cetearyl alcohol; cetyl alcohol; cetereth-20; panthenol; hydrolyzed animal protein; isostearyl ethylimidonium ethosulfate; dimethyl lauramide oleate; honey; wheat germ oil; stearalkonium chloride, hydroxyethylcellulose, dimethicone, citric acid, fragrance, methylparaben, DMDM hydantoin, Red 4, and Yellow 10.

The patent literature is also replete with many hundreds of references to hair preparations. A LEXPAT (trademark of Mead Data Central) patent data base search for "damaged hair" revealed 105 hits. While not intended to be illustrative of the state of the art, the following is a sampling of the aforementioned 105 "hits".

U.S. Pat. No. 4,061,150 of Dasher et al (and recited on the label of the Alberto VO5 product mentioned above) teaches a pretreatment preceding shampooing with anionic type hair shampoos, which pretreatment utilizes readily water-soluble quaternary ammonium compounds in combination with oils and other supplemental ingredients.

U.S. Pat. No. 4,067,345 issued to Ralph Kelly and assigned to Cincinnati Milicron Inc. relates to compositions for retarding chemical damage to hair having as protective agents organic compounds containing at least two or more polar groups, e.g. carboxyl groups, which are separated by at least 15 atoms the majority of which are carbon atoms and preferably containing a cyclic moiety of at least 5 atoms, e.g. the dimer of linoleic acid.

U.S. Pat. Nos. 4,774,075 and 4,828,819, each to Lang et al and assigned to L'Oreal) disclose compositions for the treatment of keratin materials containing a specified class of bis-(quaternary ammonium) derivatives.

U.S. Pat. No. 4,900,545 issued to Wisotzki et al discloses a composition for the regeneration of hair split ends in an aqueous or aqueous/alcoholic solution or emulsion containing panthenol, at least one mono- or di-saccharide, and, optionally, polyvinylpyrrolidone and/or a triol.

Finally, U.S. Pat. No. 4,996,059 of Grollier et al and assigned to L'Oreal relates to a composition for the treatment of keratin substances containing at least one amphoteric polymer having (A) units derived from a monomer containing at least one basic nitrogen atom; and (B) units derived from an acid monomer containing one or more carboxyl or sulphonyl groups, or alternatively, A and B can denote groups derived from zwitterionic carboxybetaine monomer; A and B can also denote a cationic polymer chain containing secondary or tertiary amine groups having a carboxyl or sulphonyl group joined via a hydrocarbon radical, or, alternatively, A and B form part of a chain of a polymer with alpha, betadicarboxyethylene units, in which one of the carboxyl groups has been reacted with a polyamine containing one or more primary or secondary amine groups, and at least one cationic polymer of the polyamine or poly-(quaternary ammonium) type, containing amine or ammonium groups in the polymer chain or joined to the latter.

From the foregoing survey selected at random it will thus be abundantly clear that the hair treatment art is an exceedingly crowded art with a wide assortment of ingredients asserted to be effective.

Notwithstanding the current state of the art, there still remains a great need for improved procedures for protecting keratin-containing substances, particularly hair, against damage and to help restore the damaged keratinous substances to a healthy condition.

Stated simply, it is to this task to which the present invention is directed.

BRIEF DESCRIPTION OF THE INVENTION

In accordance with one embodiment of the present invention, novel prophylactic compositions are provided comprising an oleophilic vehicle, preferably a liquid fatty acid vehicle containing therein a long chain alkane for bonding hydrophobically to keratin, which compositions are particularly well suited for home use. In another embodiment of the invention directed primarily for use in salons, the above-mentioned compositions will additionally contain a dibasic long chain aliphatic compound having hydrogen bonding or crosslinking sites on both ends. In either of the compositions, the liquid fatty acid permeates the keratinous material so that the prophylactic composition treats the keratinous material internally to protect and/or to restore it to a healthy state, as distinguished from prior formulations which when applied topically can only affect a surface treatment of the keratinous material.

DETAILED DESCRIPTION OF THE INVENTION

As was previously mentioned, the present invention is directed to the treatment of keratinous body materials, e.g. hair, skin and nails, to prevent damage to these materials or to help restore damaged keratinous body materials to their natural healthy state.

Since the invention is particularly directed to hair treatment, it will be described in detail hereinafter by reference thereto.

It has long been known in the art that hair fibers are easily stripped of their lipids by the chemicals routinely applied in salon treatments, e.g. shampoos, relaxants, bleaches and colorants. Yet, it has only recently been appreciated that lipids and lipophilic moities may play a structural role within the dense, practically impenetrable hair matrix.

The other source of damage is mechanical insult resulting in destruction of certain levels of structure within the keratin network. As will be discussed in detail hereinafter, methods are known for observing this destruction.

The present invention is initially predicated on the hypothesis that in order to treat hair properly it is first necessary to understand very clearly the complex structure and morphology of the components of hair fibers.

Basically, a hair fiber is composed of various elements of keratin organized in the long axis of the fiber. Keratin chains are generally alpha helical with several orders of structure including macroscopic bundles. These levels of organization are stabilized through covalent (disulfide crosslinks), ionic, and secondary valence forces. Mechanical and/or chemical damage is characterized by disruption of these interactions to a point at which the macroscopic network is weakened. Loss of strength manifests as increased swelling in water, increase in diffusibility of other solutes and solvents, and other changes.

In accordance with the present invention, mechanical and chemical damage, as manifested by the above-mentioned changes, may be obviated and/or treated by applying to the hair, preferably at slightly elevated temperatures, a composition comprising an oleophilic liquid vehicle for penetrating within the hair fiber, which vehicle contains at least a higher straight chain or n-alkane, e.g. an n-alkane containing at least 16 carbon atoms for bonding hydrophobically to keratin. For optimum results the composition will additionally contain a long chain dibasic acid.

As distinguished from the aqueous compositions heretofore known in the art and which only slowly penetrate the dense hair structure, the oleophilic vehicle and ingredients penetrate into the hair shaft, thereby infusing the other reagents in the vehicle into the hair shaft and particularly to the damaged sites within the hair shaft.

The preferred oleophilic vehicle comprises a free fatty acid or a mixture of free fatty acids which occur naturally in keratinous substances of the body, e.g. hair, skin and nails. In this context, the oleophilic vehicle will serve the further function of restoring natural useful constituents.

Oleic and palmitic acids are the most abundant free fatty acids in skin, sebum and hair. They account for 50–70 percent of the total free fatty acid content as well as 15–20 percent of the total natural lipid fraction of these biological materials. Accordingly, oleic acid or a mixture of oleic acid and palmitic acid is preferred as the liquid vehicle, most preferably along with a lesser amount of linoleic ($C_{18:2}$) acid which occurs in nature to a lesser extent. For instance, it is postulated that one may combine these ingredients in proportion to their natural abundance in human epidermis, e.g. oleic acid = 50% by total weight; palmitic acid = 30% by total weight; and linoleic acid = 20% by total weight. However, no benefit has yet been ascertained by matching natural abundance ratios.

While the oleophilic vehicle will preferably comprise a fatty acid or a mixture of fatty acids, as previously discussed, the oleophilic vehicles contemplated for use in the present invention are not restricted thereto.

As examples of other oleophilic materials contemplated by this invention, mention may be made of fatty alcohols such as oleyl alcohol; fatty acid esters such as methyl oleate or ethyl oleate; glyceryl esters of fatty acids such as glyceryl monooleate, glyceryl dioleate, glyceryl trioleate (triolein), glyceryl monolinoleate, etc.

It is theorized that the glyceryl esters may be particularly efficacious in that they will be hydrolyzed within the keratin matrix to release free fatty acids, thus providing an ideal method for incorporating a fatty acid. On the other hand, if fatty alcohols are utilized in the oleophilic vehicle, they will also serve to provide a hydrogen bonding function, an essential part of this invention to be discussed in detail hereinafter.

The higher n-alkane in the novel prophylactic composition of this invention diffuses into the hair shaft, particularly at sites of damage where it can be observed by polarizing microscopy (as will be discussed in detail hereinafter) within the voids of the hair shaft cortex. There, the higher or long chain alkane is available to bond hydrophobically to the keratin (protein chain) and in this manner forms hydrophobic associations. This may proffer a resistance to matrix swelling in water (which is further damaging to the hair) as well as resistance to alkaline solutions such as those commonly introduced in the home and salon.

While various higher alkanes (paraffinic hydrocarbons) having at least eighteen carbon atoms may be employed, preferred again are those which are naturally occurring.

It has been shown that hair contains a collection of n-alkanes which make up about 6 percent of the neutral lipid fraction. These range from octadecane ($C_{18}H_{38}$; m.p. 28° C.) to pentatriacontane (($C_{35}H_{72}$; m.p. 75° C.).

Although all of these can be used in varying amounts in the present invention, the preferred n-alkane is eicosane ($C_{20}H_{42}$; a colorless waxy solid, m.p. 37° C., insoluble in water but soluble in alcohol), because it melts near body temperature and therefore maintains mobility within the hair shaft, even in locally high concentration.

The preferred dibasic acid is sebacic acid, a long chain diacid of the formula:

$$HOOC-(CH_2)_8-COOH$$

Ammonium salts of this diacid have been shown to raise the shrinkage temperature of collagen through several postulated linkages. Sebacic acid has also been used to block amine functional groups, and, in combination with oleic acid, to "moisturize" skin. As used in the compositions of the present invention, it serves as a difunctional crosslinking agent. Such an agent would ideally reinforce keratin chains at functional groups exposed by structural damage. It will additionally be available for ionic bonding in its ionized form. Crosslinking would provide a retractive force opposing the swelling of the keratin matrix in water.

In formulations containing the above ingredients, the sebacic acid is only sparingly soluble in the liquid fatty acid vehicle. Accordingly, no more than about two percent sebacic acid can be employed, any excess over this amount being non-diffusible within the hair fibers.

It has been found, however, that the addition of a fourth ingredient, SD alcohol, serves to increase the level of dissolved sebacic acid in the formulation. Additionally, the alcohol acts as a penetration enhancer.

While the foregoing constitutes the essential ingredients of the prophylactic compositions of this invention, it will be appreciated that other reagents providing specific desired functions may optionally be included. By way of example, the formulation may additionally contain one or more oil-soluble antioxidants, vitamins, fragrances, and/or other reagents of interest. It will of course be appreciated, however, that any additional ingredients should be innocuous in the sense that they do not adversely affect the ability of the formulation to restore lipids, reinforce the keratinous matrices and potentiate self-repair over a period of time.

As was heretofore alluded to, polarizing microscopy may be employed to analyze hair for damage, evaluate the effectiveness, or lack thereof, of formulations projected to be useful in the practice of this invention to restore or repair damaged hair, hand/or to chart the progress of damaged hair treatments.

While the polarizing microscopy which may be utilized is per se old, reported in the literature and accordingly per se comprises no part of this invention, it is appropriate to discuss polarizing microscopy in some detail for a full and complete understanding of how the invention may be utilized in hair treatment.

Polarizing microscopy is in common use in fields of metallurgy, crystallography, and, to a certain extent, in polymer science and biochemistry. Although it has not been used extensively in the field of cosmetic science, applicant is aware of two reports describing its use, namely, *Birefringence: Polarization Microscopy as a Quantitative Technique of Human Hair Analysis*, Curtis, R. and Tyson, D., J. Soc. Cosmet. Chem., 27, pp 411-431 (1976); and *Polarized Light Microscopy for the Cosmetic Chemist*, Stern E., Cosmetics and Toiletries, 91, pp 50-56 (1976). More recently, applicant's published Ph. D. Dissertation (The Effects of Electrolytes on the Structure and Thermal Stability of Bovine Articular Cartilage, Etheredge, R. W. III, Northeastern University, 1985) described the use of polarizing microscopy to probe the structure of bovine cartilage and to propose a reasonable structural model based upon mechanical, optical, thermal and biochemical properties of cartilage. In all cases, predictions made based upon polarizing microscopy evidence were corroborated by other more labor intensive methods, thereby unequivocally establishing the efficacy of polarizing microscopy as a valuable tool in the field of structural investigation, apart from the fact that it is inexpensive, rapid, nondestructive and non-invasive.

In view of the foregoing, it is clear that polarizing microscopy can be useful in the cosmetic area for analyzing skin and hair. While applicant believes, without knowing, that it is currently used in various cosmetic R&D facilities, it is believed that it has never heretofore been employed in a commercial salon environment. This is at least in part due to the lack of hair care products that can address the problems revealed by this method, rendering academic or moot whether the salon personnel have the training to engage in such procedures.

With reference now to the use of polarizing microscopy in the practice of this invention for hair treatment, the keratin molecule, like collagen, demonstrates positive birefringence and can accordingly be seen in polarizing light as colored regions within the hair fiber. It is well known and reported in the literature that when the organization of microfibrils contains higher densities of fibrils, the colors change according to the Michel-Levy Color Chart, namely the colors increase or "rise" as follows:

Grey=>White=>Yellow=>Red=>Blue=->Yellow/green.

Therefore, since polarizing microscopy can essentially "see" into the hair fiber and view the supercellular organization of hair components, the present invention utilizes polarizing microscopy to observe the extent of hair damage, to determine the effect of various ingredients and formulations in preventing damage, and/or to view the progress of prophylactic compositions in restoring damaged hair to its natural healthy state.

The average growth rate of human hair is on the order of 1 cm per month. Using this as a measure of time, one can follow the development of the internal structure of hair fibers with time and view a history of environmental effects to the hair as well as certain health and dietary effects. The power of this technique becomes clear when one scans the whole length of the hair fiber and sees periodic changes in the "health" of the hair sample. For instance, nacent hair may be quite strong and display deep blue color. As this segment grows and moves away from the scalp, the newly emergent hair may develop in a different way and display lower colors such as red or yellow. These segments may also suffer environmental damage such as chlorine and peroxide exposure and mechanical abrasions and compression due to hair care stresses. Such changes in structure are seen using the method of polarizing microscopy. Improvements in hair condition, whether natural or due to hair care therapy, are also observed.

The following description illustrates how polarizing microscopy can be utilized in the salon.

The heart of any polarizing microscopy system of course is the polarizing microscope with accessory plates or filters such as quarter wave, and 530 nm run first order red. The image from the microscope is recorded by a color chip camera with high sensitivity to low light levels of exposure. This is necessary since many of the images are taken with a dark background, the so-called crossed polarizer position with no retardation plates. The camera image is passed to a high resolution monitor and into a recording device such as a videorecorder or computer with mass storage capability. For instance, a freeze-frame device commercially available from Polaroid Corporation may be used to capture the monitor image and to print out a color photograph. An optimum system would also possess an optical disk storage capability.

Since hair is elliptical in cross-section and may twist or turn over its length, it is desirable to be able to pull and rotate the hair fiber to be analyzed as one observes its structure in the microscope. Under some circumstances it may be necessary to twist or elongate the test sample while observing the changes in birefringence. The hair sample can be made to rotate freely in immersion oil while under the microscope for observation. Devices for doing this per se comprise no part of this invention and accordingly need not be discussed further.

There are certain chemical probes that are useful in conjunction with polarizing microscopy in diagnosing problems associated with hair care.

For instance, a hair fiber with a section which has suffered mechanical damage will appear under the polarizing microscope as having a break in the blue color. A denaturing solution such as 1M urea in 0.75M sodium hydroxide may be applied to the hair. The damaged segment is attacked very quickly by the solution and becomes denatured long before the undamaged shaft. Using this denaturant, an entire undamaged shaft can be probed for subtle differences in strength as described hereinafter.

The rate of permeation of the denaturant is inversely proportional to the density of microfibrils within the fiber. Segments with greater blue color density denature last. Those with less blue color are denatured first. The overall time necessary to fully denature the fiber (about 10-12 minutes) is another measure of strength. Intrinsically weak areas are revealed during the denaturation process.

The following procedure illustrates the protocol that may be employed in hair salons in order to characterize hair fibers and thereafter recommend formulations to address the hair care needs of their clients in accordance with this invention.

Promptly after entering the salon, several (e.g. 3-5) hair fibers are taken from the client by cutting as close to the scalp as possible. The samples are then immersed in a peroxide oxidizing solution to oxidize the melanin or hair color in order to allow unobstructed viewing of internal structural features. The hair samples are then examined under the polarizing microscope as previously described for the following features:

1. average thickness and uniformity;
2. condition of the cuticle or scale at the surface;
3. general appearance of the internal structure;
4. areas of weakness or damage;
5. areas of weakness revealed by the chemical probe; and
6. intrinsic deformities and anomalous features such as crimps, knots, twists, turns, etc.

The analysis is recorded on videotape with or without a narrative provided by the technician. A representative photograph is taken that graphically presents the overall "health" of the person's hair. This photograph may then be affixed in a brochure or simplified report to be given the client.

During any other treatments the client is receiving in the salon or immediately thereafter, the client is interviewed. Within a space of about five minutes the results of the hair analysis are shared with the client, giving the client a copy of the test results and optionally showing the client the video version of the results. Most importantly, hair care formulations are recommended to the client to address any damages or deficiencies which may be uncovered. The client should also be advised that the condition of the hair changes during the year with fluctuations in climate, health of the client, changes in grooming habits, etc. For this reason, a periodic examination is suggested to allow the proper follow-up. Finally, the client may be made aware that the salon maintains an individual "health" record for the clients so that product recommendations may be tailored to the individual client's changing needs.

The novel health care formulation of this invention may be applied following the above-mentioned analysis or, alternatively, it may be applied routinely whenever a client enters the salon for hair care.

By way of illustration, it may be applied prior to shampooing. Heat can be used to accelerate diffusion of the reagents into the hair and scalp. If applied at room temperature, diffusion into the hair and scalp will be essentially completed in on the order of 15-20 minutes. However, when the formulation is warmed prior to applying or, if applied at room temperature, a hot towel is wrapped around the hair, the diffusion time may be shortened somewhat, e.g. to 10-15 minutes. In either case, after the prescribed time (which on the safe side may be on the order of 20 minutes), the excess treatment formulation is shampooed from the hair and normal salon treatment is resumed.

The following example relates to hair analysis site trials conducted on a population sampling.

EXAMPLE 1

Limited trials were conducted on 33 clients at a main salon in Boston, Mass. Activity at this salon is reportedly 1000-2000 customers per week. Since the salon is in proximity to Boston University (and easily accessible to Boston College, Harvard and M.I.T.) it is perceived to be possible that the test population was skewed somewhat to younger age groups. In any case, 89% of the volunteer participants were stated to be between 20 and 39 years old. A good cross-section of hair types was seen across this limited age group sampling. The cross-section included hair of all natural colors, chemically treated and untreated, and hair with very specific problems. Participants were categorized as to overall hair strength. However, strength was not found to be related to permanence or retention of hair in the scalp, since several people with otherwise "strong" hair experienced excessive hair loss. Moreover, from this initial sampling there does not appear to be any correlation between strength and damage to the hair, although a correlation between manageability and strength may exist. Examination of hair samples under the polarizing microscope in the described manner revealed structural damage in 13 of the 33 participants tested. This clearly was indicative of the present need in the hair management art for formulations which would be at the very least protect damaged areas from further insult and which ideally should also work to reverse this damage.

TABLE 1

| SUBJECT | AVERAGE HAIR DIAMETER | COLOR RANKING | DAMAGES PER LENGTH (INCHES) | COMMENTS |
| --- | --- | --- | --- | --- |
| 1 | 71 MICRONS | 4 | 0 (12) | THICK CUTICLE |
| 2 | 92 | 1 | 0 (24) | ASYMMETRIC TWISTING |
| 3 | 81 | 5 | 0 (24) | SOME TWISTING |
| 4 | 50 | 3 | 0 (9) | INCONSISTENT/KINKS |
| 5 | 77 | N.A. | 8 (12) # | INCONSISTENT/TWISTS |
| 6 | 91 | 1 | 0 (18) | GENTLE TWISTING |
| 7 | 57 | 1 | 0 (12) (1) | TWISTS |
| 8 | 64 | 3 | 1 (9) # | STRAIGHT |
| 9 | 93 | 4 | 0 (7) | TWISTS |
| 10 | 74 | 4 | 0 (13) | TWISTS |
| 11 | 132 | 4 | 0 (12) | STRAIGHT |
| 12 | 69 | 5 | 6 (18) # | STRAIGHT/FINE |
| 13 | 65 | 4 | 0 (18) | |
| 14 | 54 | 4 | 0 (18) | RAPID TWISTS/TURNS |
| 15 | 121 | 4 | 0 (9) | |
| 16 | 89 | 4 | 0 (6) | TURNS |
| 17 | 54 | 3 | 0 (12) ## | BREAKAGE/PITTING |
| 18 | 64 | 3 | 0 (8) | TURNS |
| 19 | 81 | 5 | 1 (36) # | SPLIT SHAFTS |
| 20 | 97 | 5 | 0 (18) # | CHEMICAL DAMAGE! |
| 21 | 100 | 3 | 1 (20) # | STRAIGHT/CONSISTENT |
| 22 | 74 | 3 | 1 (18) # | |
| 23 | 80 | 2 | 2 (9) # | TWISTS/TURNS |
| 24 | 105 | 5 | 0 (15) (33) | INCONSISTENT |
| 25 | 90 | 5 | 0 (11) | WEAK AREAS |
| 26 | 87 | 4 | 4 (15) # | INCONSISTENT |
| 27 | 82 | 4 | 0 (15) | INCONSISTENT |
| 28 | 77 | 5 | 0 (9) | |
| 29 | 80 | 3 | 5 (14) # | |
| 30 | 93 | 5 | 6 (20) # | KINKS/ABRASIONS |
| 31 | 85 | 5 | 2 (6) # | WIDE MEDULLA |
| 32 | 70 | 5 | 0 (6) | |
| 33 | 85 | 4 | 0 (15) | CONSISTENT |

KEY
1. "#" marks samples found to be damaged
2. "1" marks subject with strongest hair
3. "33" marks subject with weakest hair
4. Color index is a measure of strength. The index is based on the color observed during analysis. Lowest number = highest strength as follows:
BG(X) > Bg(X) > B(X),B-(X) > R(X),Bg($\frac{1}{4}$) > B($\frac{1}{4}$), B-($\frac{1}{4}$) > R($\frac{1}{4}$)
1 > 2 > 3 > 4 > 5 > 6
B = BLUE, G = GREEN, g = MINOR AMOUNTS OF GREEN, "-" = LESSER AMOUNTS, R = RED, (X) = CROSSED POLARIZERS, ($\frac{1}{4}$) = QUARTER WAVE FILTER As seen, in this random sampling 13 of 33 subjects (39%) exhibited varying degrees of hair damage.

From this sampling, it can be postulated that on the day tested, 39 percent of the subjects were in need of treatment to prevent further damage and to help restore those areas exhibiting damage, However, it does not follow a fortiori that the remaining 61% require no treatment. Rather, it is postulated that treatment across the board is warranted as a preventative measure against hair damage which may be manifested another day, e.g. following bleaching, coloring, the other salon treatments as well as physical damage, climate changes and the like.

The following examples relate to the preparation of illustrative formulations contemplated by this invention.

EXAMPLE 2

A hair care formulation:

| | |
| --- | --- |
| Isopropanol | 77.50 weight percent |
| Sebacic Acid | 3.75 weight percent |
| Eicosane | 3.75 weight percent |

-continued

| | |
| --- | --- |
| Oleic Acid NF* | 15.00 weight percent |

*National Formulary grade was prepared by first heating a solution of the isopropanol and sebacic acid to a temperature of 34° C., thereafter adding the eicosane with stirring and after dissolution adding the oleic acid and stirring until mixed.

If desired, one may then add drops of aromatic oils or other nonaggression fragrances according to individual whim.

\* National Formulary grade

EXAMPLE 3

A hair care formulation:

| | |
| --- | --- |
| Isopropanol | 86.50 weight percent |
| Sebacic Acid | 1.75 weight percent |
| Eicosane | 1.75 weight percent |
| Oleic Acid NF | 10.00 weight percent | was prepared in the manner described in Example 2.

EXAMPLE 4

A hair formulation:

| | |
| --- | --- |
| Oleic Acid NF | 70.00 weight parcent |

-continued

| | |
|---|---|
| Eicosane | 30.00 weight percent | was prepared by heating the oleic acid to about 40° C. and then adding the eicosane with stirring until it was fully dissolved in the oleic acid. Again, aromatic oil or fragrance may be added, as desired.

EXAMPLE 5

A hair formulation:

| | |
|---|---|
| Oleic Acid NF | 53.50 weight percent |
| Ethanol SD | 26.40 weight percent |
| Eicosane | 13.40 weight percent |
| Sebacic Acid | 6.70 weight percent |
| Oil Based Fragrance | trace | was prepared by heating the oleic acid to 40° C. and then dissolving the eicosane in the heated oleic acid. The sebacic acid was dissolved in the ethanol and the resulting solution was then added to the oleic acid solution. The fragrance was then added and the formulation was then allowed to cool. It is to be noted that sebacic acid is only miscible in oleic acid at a ratio no greater than 1:50. In this example, the alcohol is necessary to dissolve the excess sebacic acid so that it can be carried into the hair.

EXAMPLE 6

A hair formulation:

| | |
|---|---|
| Oleic Acid NF | 83.60 weight percent |
| Eicosane | 14.75 weight percent |
| Sebacic Acid | 1.65 weight percent | was prepared by heating the oleic acid to 40° C. and adding the sebacic acid with stirring until fully dissolved. The eicosane was added to the resulting solution with stirring to dissolve. Optionally, antioxidant to prolong shelf life, fragrance, colorants, etc. may be added and the resulting formulation then cooled. In this example, it will be noted that since the concentration of sebacic acid is within the 1:50 ratio, alcohol is not required.

The following examples illustrate methods for applying the novel hair formulations of this invention.

EXAMPLE 7

Approximately 25.0 ml of the formulation prepared in Example 6 were applied by spray or squirt bottle to the hair before shampooing. Care is exercised to expose as much hair as possible to direct contact with the formulation, especially in distal regions. Since heat accelerates somewhat diffusion of the product into the hair, a heat lamp is beneficial in applying the formulation to the hair. Residence times in the hair should be on the order of 15-20 minutes. Asymptotic penetration has been demonstrated to occur in about one hour. The effect is cumulative and cannot be removed easily from the hair shaft by shampooing. Following application, the excess is removed from the hair surface by normal shampooing.

[Since the product has not yet been tested for scalp irritation or other dermatological effects, applicant cannot now state whether direct contact with the scalp should be minimized. Accordingly, unless it has been reported or shown to be innocuous to the scalp, caution dictates that direct contact should be minimized until such time as it is indicated safe for direct contact with the scalp. This is true for all of the disclosed formulations.]

EXAMPLE 8

Approximately 25 ml. of the formulation prepared in Example 3 were applied the same as in Example 7. However, since this formulation is of reduced strength, it is postulated that it may also be applied to damp hair followed by shampooing to remove excess.

EXAMPLE 9

The formulation prepared in Example 4 is designed as a hot oil treatment. It can be applied in the foregoing manner with or without an alcohol additive. Since it will be non-irritating to the scalp, greater amounts can be used, if desired. Fragrances can be added and delivered to damaged segments of hair, as in the other formulations. This formulation is especially suited for home use.

From the foregoing discussion it will be seen that the present invention provides novel prophylactic formulations for hair treatment, which formulations will inhibit damage to the hair as well as to help restore damaged hair to a healthy state.

Since the invention is particularly directed to hair treatment, it has been described in detail by reference thereto. However, it is contemplated that the inventive concepts described herein may also be employed in the preparation of formulations to treat other human keratinous materials, namely skin and nails, as well.

Since certain changes may be made without departing from the scope of the invention herein contemplated, it is intended that the descriptive matter set forth in the foregoing specification, including the examples, be taken as illustrative and not in a limiting sense.

What is claimed is:

1. A prophylatic composition for permeating within keratinous body material to treat the keratinous material internally to protect and/or to restore it to a healthy state, the composition comprising effective amounts of the following ingredients:

(1) from about 10.00 to about 83.60 percent by weight of an oleophilic vehicle for permeating within the keratinous body material;
  (2) from about 1.75 to about 30.00 percent by weight of reagent which when transported within the keratinous body material in the oleophilic vehicle will bond hydrophobically to the keratin in the keratinous body material, the reagent comprising at least one n-alkane compound having at least eighteen carbon atoms;
  (3) from about 1.65 to about 6.70 percent by weight of long chain aliphatic compound of at least eight carbon atoms having hydrogen bonding or crosslinking sites at both ends;
  (4) from about 0.00 to about 26.40 percent by weight of SD alcohol; and
  (5) from about 0.00 to about 86.50 percent by weight of SD isopropanol.

2. A composition as defined in claim 1 wherein the oleophilic vehicle comprises oleic acid.

3. A composition 2 wherein the aliphatic compound having hydrogen bonding or crosslinking sites at both ends is an alpha, omega-dibasic acid.

4. A composition as defined in claim 24 wherein the dibasic acid is sebacic acid.

5. A composition for permeating keratinous body material to treat the keratinous material internally, comprising an effective amount of oleophilic vehicle for permeating the keratinous body material, the vehicle containing an effective amount of reagent for bonding hydrophobically to keratin.

6. A composition as defined in claim 5 wherein the oleophilic vehicle comprises at least one fatty acid, fatty alcohol and/or glyceryl ester of a fatty acid.

7. A composition as defined in claim 5 wherein the oleophilic vehicle comprises at least one liquid fatty acid.

8. A composition as defined in claim 5 wherein the reagent for bonding hydrophobically to keratin comprises at least one n-alkane containing at least sixteen carbon atoms.

9. A composition as defined in claim 5 wherein the vehicle also contains an effective amount of a long chain aliphatic compound of at least eight carbon atoms having hydrogen bonding or crosslinking sites on both ends.

10. A composition as defined in claim 9 wherein the aliphatic compound is an alpha, omega- dibasic acid.

11. A composition as defined in claim 5 wherein the oleophilic vehicle consists of at least one free fatty acid which occurs naturally in body keratinous materials.

12. A composition as defined in claim 10 wherein the dibasic acid is sparingly soluble in the oleophilic vehicle and the composition further includes SD alcohol in an amount sufficient to increase the amount of dibasic acid soluble in the composition.

13. A composition for permeating keratinous body material to treat the keratinous material internally, comprising an effective amount of an oleophilic vehicle for permeating the keratinous material, the olephilic vehicle consisting of at least one free fatty acid which occurs naturally in the keratinous body material, the oleophilic vehicle containing an effective amount of reagent which when transported within the keratinous body material will bond hydrophobically to the keratin in the keratinous body material, the reagent consisting of at least one n-alkane having at least eighteen carbon atoms.

14. A composition as defined in claim 13 wherein the oleophilic vehicle is selected from the group consisting of oleic acid, a mixture of oleic and palmitic acids and a mixture of oleic, palmitic and linoleic acids.

15. A composition as defined in claim 14 wherein the alkane comprises eicosane.

16. A composition as defined in claim 13 wherein the oleophilic vehicle further contains an aliphatic compound of at least eight carbon atoms having hydrogen bonding or crosslinking sites on both ends.

17. A composition as defined in claim 16 wherein the aliphatic compound is sebacic acid.

18. A composition as defined in claim 17 wherein the oleophilic vehicle is selected from the group consisting of oleic acid, a mixture of oleic and palmitic acids and a mixture of oleic, palmitic and linoleic acids.

19. A composition as defined in claim 18 wherein the alkane comprises eicosane.

20. A composition as defined in claim 18 wherein the amount of sebacic acid in the composition is no greater than about two percent by weight.

21. A composition as defined in claim 19 including SD alcohol and the sebacic acid is present in an amount greater than two percent by weight.

22. The method for treating hair on a human's head comprising the steps of:
applying to the hair a composition comprising an effective amount of an oleophilic vehicle for permeating within the hair, the vehicle containing an effective amount of reagent for bonding hydrophobically to keratin;
allowing the composition to diffuse into the hair and scalp; and
thereafter removing excess composition which has not diffused into the hair and scalp.

23. The method as defined in claim 22 wherein the composition further includes an aliphatic compound of at least eight carbon atoms having hydrogen bonding or crosslinking sites on both ends.

24. The method as defined in claim 22 including the intermediate step of warming to accelerate the diffusion of the reagents into the hair and scalp.

25. The method as defined in claim 22 including the preliminary step of analyzing a sample of the hair under a polarizing microscope to determine damage to the hair and deficiencies prior to applying the composition.

* * * * *